US010173961B2

(12) United States Patent
Moonen et al.

(10) Patent No.: US 10,173,961 B2
(45) Date of Patent: Jan. 8, 2019

(54) PROCESS FOR THE REDUCTIVE AMINATION OF HALOGEN-CONTAINING SUBSTRATES

(71) Applicant: Taminco BVBA, Ghent (BE)

(72) Inventors: Kristof Moonen, Hamme (BE); Kim Dumoleijn, Eede (NL); Laura Prati, Milan (IT); Alberto Villa, Pozzuolo Martesana (IT)

(73) Assignee: Taminco BVBA, Ghent (BE)

( * ) Notice: Subject to any disclaimer, the term of this patent is extended or adjusted under 35 U.S.C. 154(b) by 0 days.

(21) Appl. No.: 15/523,864

(22) PCT Filed: Nov. 4, 2015

(86) PCT No.: PCT/EP2015/075734
§ 371 (c)(1),
(2) Date: May 2, 2017

(87) PCT Pub. No.: WO2016/071410
PCT Pub. Date: May 12, 2016

(65) Prior Publication Data
US 2017/0320812 A1    Nov. 9, 2017

(30) Foreign Application Priority Data

Nov. 4, 2014 (EP) ..................................... 14191761

(51) Int. Cl.
| A01N 37/42 | (2006.01) |
| C07B 43/04 | (2006.01) |
| C07C 209/26 | (2006.01) |
| C07C 211/29 | (2006.01) |
| C07C 249/04 | (2006.01) |

(52) U.S. Cl.
CPC ............ *C07C 209/26* (2013.01); *A01N 37/42* (2013.01); *C07B 43/04* (2013.01); *C07C 211/29* (2013.01); *C07C 249/04* (2013.01)

(58) Field of Classification Search
CPC ..... C07B 43/04; C07C 209/26; C07C 211/29; C07C 249/04
See application file for complete search history.

(56) References Cited

U.S. PATENT DOCUMENTS

| 3,499,034 A | 3/1970 | Gonzalez |
| 3,546,297 A | 12/1970 | Kosak |
| 3,666,813 A | 5/1972 | Hindin et al. |
| 3,830,756 A | 8/1974 | Sanchez et al. |
| 4,024,274 A | 5/1977 | Druckrey et al. |
| 5,011,996 A | 4/1991 | Kiel et al. |
| 5,512,529 A | 4/1996 | Deller et al. |
| 5,689,021 A | 11/1997 | Cordier et al. |
| 6,410,806 B2 | 6/2002 | Oku et al. |
| 6,429,335 B1 | 8/2002 | Kiel |
| 6,462,236 B2 | 10/2002 | Liang et al. |
| 7,230,134 B2 | 6/2007 | Borner et al. |
| 2001/0056035 A1 | 12/2001 | Auer et al. |
| 2007/0078282 A1 | 4/2007 | Schramm et al. |
| 2010/0113778 A1 | 5/2010 | Wiegand et al. |
| 2010/0274054 A1 | 10/2010 | Staeb et al. |
| 2016/0002146 A1 | 1/2016 | Peters et al. |
| 2016/0207874 A1 | 7/2016 | Moonen et al. |
| 2017/0129847 A1 | 5/2017 | Moonen et al. |

FOREIGN PATENT DOCUMENTS

| CN | 102503836 A | 6/2012 |
| EP | 0 312 253 A2 | 4/1989 |
| EP | 1 195 192 A1 | 4/2002 |
| EP | 2 774 911 A1 | 9/2014 |
| GB | 2 024 643 A | 1/1980 |
| GB | 2 301 660 A1 | 3/2011 |
| WO | WO 2013/017611 A1 | 2/2013 |
| WO | WO 2014/135508 A1 | 9/2014 |
| WO | WO 2014/202436 A1 | 12/2014 |
| WO | WO 2014/202441 A1 | 12/2014 |

(Continued)

OTHER PUBLICATIONS

Gomez et al., "The Reductive Amination of Aldehydes and Ketones and the Hydrogenation of Nitriles: Mechanistic Aspects and Selectivity Control," Adv. Synth. Catal. 2002, 344(10), 1037-1057 (Year: 2002).*

Cheng et al., "The effect of water on the hydrogenation of o-chloronitrobenzene in ethanol, n-heptane and compressed carbon dioxide", Applied Catalysis A: General 455, (2013), pp. 8-15.

Dan-Qian et al, "Hydrogenation of ionic liquids: An alternative methodology toward highly selective catalysis of halonitrobenzenes to corresponding haloanilines", Journal of Molecular Catalysis A: Chemical, 235, (2005), pp. 137-142.

Kratky et al, "Effect of catalyst and substituents on the hydrogenation of chloronitrobenzenes", Applied Catalysis A: General, 235, (2002), pp. 225-231.

(Continued)

*Primary Examiner* — Pancham Bakshi
*Assistant Examiner* — Mark R Luderer
(74) *Attorney, Agent, or Firm* — Dennis V. Carmen

(57) ABSTRACT

Disclosed is a process for performing a reductive amination of a first functional group in an organic feed substrate, which feed substrate comprises at least one further functional group containing a halogen atom, wherein the halogen atom is selected from the list consisting of chlorine, bromine, iodine, and combinations thereof, in the presence of hydrogen and a heterogeneous catalyst comprising at least one metal from the list of Pd, Pt, Rh, Ir, and Ru, and in absence of any catalytic amount of any second metal from the list consisting of Ag, Ni, Co, Sn, Bi, Cu, Au, and combinations thereof. The process is preferably applied for the reductive amination of 2-chloro-benzaldehyde to form 2-chloro-benzyldimethylamine, as an intermediate in the production of active agrochemical compounds and microbicides of the methoximinophenylglyoxylic ester series.

25 Claims, No Drawings

(56) References Cited

FOREIGN PATENT DOCUMENTS

| WO | WO 2015/032653 A1 | 3/2015 |
|---|---|---|
| WO | WO 2016/071410 A1 | 5/2016 |

OTHER PUBLICATIONS

Wang et al., "A green synthesis route of ortho-chloroaniline: Solvent-free selective hydrogenation of ortho-chloronitrobenzene over Pt—Ru/ $Fe_3O_4$/C catalyst", Catalysis Communications, vol. 19, (2012), pp. 110-114.

Mahata et al., "Promotional effect of Cu on the structure and chloronitrobenzene hydrogenation performance of carbon nanotube and activated carbon supported Pt catalysts", Applied Catalysis A: General 464-465, (2013), pp. 28-34.

Han et al., "Effect of transition metal (Cr, Mn, Fe, Co, Ni and Cu) on the hydrogenation properties of chloronitrobenzene over Pt/$TiO_2$ catalysts", Journal of Molecular Catalysis A: Chemical, 209, (2004), pp. 83-87.

Coq et al.; "Influence of alloying platinum for the hydrogenation of p-chloronitrobenzene over PtM/$Al_2O_3$ catalysts with M=Sn, Pb, Ge, Al, Zn", Journal of Molecular Catalysis, vol. 71, Issue 3, Feb. 1, 1992, pp. 317-333.

Tijani et al., "Hydrogenation of para-chloronitrobenzene over supported ruthenium-based catalysts", Applied Catalysis, vol. 76, issue 2, Sep. 16, 1991, pp. 255-266.

Cárdenas-Lizana et al., "Pd-promoted selective gas phase hydrogenation of p-chloronitrobenzene over alumina supported Au", Journal of Catalysis, vol. 262, (2009), pp. 235-243.

Bhattacharyya, "A high throughput synthesis of N,N-dimethyl tertiary amines", Synthetic Communications, vol. 30, No. 11, (2000), pp. 2001-2008.

PCT International Search Report and Written Opinion of the International Searching Authority dated Dec. 17, 2014 for International Application No. PCT/EP2014/068083.

PCT Second Written Opinion of the International Preliminary Examining Authority dated Sep. 8, 2015 for International Application No. PCT/EP2014/068083.

European Patent Application No. 13173233.1 filed Jun. 21, 2013; Applicant: BASF SE (Machine Translation).

European Patent Application No. 14151747.4 filed Jan. 20, 2014; Applicant: BASF SE (Machine Translation).

Co-pending U.S. Appl. No. 14/914,744, filed Feb. 26, 2016; Moonen et al.

Office Action dated Dec. 13, 2016 received in co-pending U.S. Appl. No. 14/914,744.

Co-pending U.S. Appl. No. 15/344,846, filed Nov. 7, 2016; Moonen et al.

Bagal et al.; "PS-Pd-NHC: an efficient and heterogeneous recyclable catalyst for direct reductive amination of carbonyl compounds with primary / secondary amines in aqueous medium"; Catalysis Science & Technology; 2012; 2; pp. 354-358.

Drinkel et al.; "Zwitterionic-Surfactant-Stabilized Palladium Nanoparticles as Catalysts in the Hydrogen Transfer Reductive Amination of Benzaldehydes" The Journal or Organic Chemistry; 2014; 79; pp. 2574-2579.

Wang et al.; "Single-phase bimetallic system for the selective oxidation of glycerol to glycerate"; Chem. Commun. (The Royal Society of Chemistry); 2006; pp. 1956-1958.

Enache et al.; "Solvent-Free Oxidation of Primary Alcohols to Aldehydes Using Au—Pd/$TiO_2$ Catalysts"; Science; 2006; vol. 311; pp. 362-365.

PCT International Search Report and Written Opinion of the International Searching Authority dated Apr. 26, 2017 for International Application No. PCT/IB2016/001904.

PCT International Search Report and Written Opinion of the International Searching Authority dated Jan. 25, 2016 for International Application No. PCT/EP2015/075734.

Office Action dated Jul. 9, 2018 received in co-pending U.S. Appl. No. 15/344,846.

Notice of Allowance dated Aug. 10, 2017 received in co-pending U.S. Appl. No. 14/914,744.

Office Action dated Feb. 7, 2018 received in co-pending U.S. Appl. No. 14/914,744.

Co-pending U.S. Appl. No. 15/678,183, filed Aug. 16, 2017; Moonen et al.

Office Action dated May 31, 2018 received in co-pending U.S. Appl. No. 15/678,183.

Notice of Allowance dated Aug. 16, 2018 received in co-pending U.S. Appl. No. 14/914,744

* cited by examiner

PROCESS FOR THE REDUCTIVE AMINATION OF HALOGEN-CONTAINING SUBSTRATES

CROSS REFERENCE TO RELATED APPLICATIONS

This application is the national stage filing under 35 U.S.C. § 371 of PCT/EP2015/075734, filed Nov. 4, 2015, which claims priority to European Application EP 14191761.7, filed Nov. 4, 2014, the contents of which are incorporated herein by reference in their entirety.

PARTIES TO JOINT RESEARCH AGREEMENT

Inventions disclosed or claimed herein were made pursuant to a Joint Research Agreement between Taminco Italia srl and Universita delgi Studi de Milano.

FIELD OF THE INVENTION

The present invention relates to chemical reactions which involve the chemical conversion of a first functional group in an organic feed substrate, in the presence of hydrogen, whereby the organic feed substrate comprises at least one further functional group containing a halogen atom other than fluorine. More particularly, the invention relates to the noble metal catalysed reductive amination of only the first functional group on the substrate while keeping the further functional group containing the halogen atom substantially untouched and present in the reaction product.

BACKGROUND OF THE INVENTION

The selective conversion of one functional group in a multifunctional feed substrate has been an area of continuous high interest throughout the chemical, pharmaceutical and agrochemical industry. In particular, halogen atoms are often incorporated next to other functional groups in active ingredients or in precursors of those active ingredients.

The objective of high selectivity has often been rather elusive, because most processes are prone to side reactions leading to significant amounts of byproducts. These side reactions are consuming valuable amounts of feed substrate, and the byproducts are often rather useless. Some of the byproducts may also be difficult to separate from the desired product. In cases where the desired product is an intermediate for the production of a further derivative, some of the byproducts may also be disturbing for further synthesis steps because they may be reactive in such downstream process step and may lead to undesired additional consumption of valuable raw materials and even to undesirable and/or unacceptable end product contamination.

Multi-step synthesis protocols of complex multifunctional chemicals more and more comprise catalytic conversion steps as these often outperform their stoichiometric alternatives with respect to atom efficiency and reduced waste generation. Reductive conversion steps with hydrogen gas as the reducing agent typically use metal based catalysts in order to proceed at rates of commercial interests.

Metals, however, often interfere with carbon-halogen bonds in organic compounds. Pd in particular is for instance capable of inserting into a carbon-halogen bond. Such behaviour is desired in its use as catalyst in so-called coupling reactions. Such reactions are often used as key steps in multi-step synthesis paths for complex organic compounds, such as active ingredients in pharmaceutical or agrochemical industry. In a coupling reaction, a halogen containing first fragment is coupled with a second fragment by means of a catalyst, in which the second fragment is coupled to the first fragment at the position where the halogen was originally located. The second fragment may be coupled via a large variety of functional groups, and different versions of such coupling reactions have often received specific names, such as the Heck coupling, which is using an olefin, the Sonogashira coupling, which is using an alkyne, the Suzuki coupling, which is using a boronic acid and the Stille coupling, which uses an alkyl tin group. This list is far from exhaustive, because many more different functional groups may possibly be used for such coupling.

Insertion of a metal such as Pd into a carbon-halogen bond in the presence of hydrogen but in the absence of a suitable fragment to couple usually results in the displacement of the halogen atom by a hydrogen atom and hence the loss of the halogen (X) as part of the substrate. Such hydrogenolysis reaction is especially enhanced in the presence of a base which may capture the liberated acid HX. This reaction may be used advantageously in some applications, such as environmental treatment of halogenated organic pollutants.

For the production of the halogenated fragments to be used in subsequent coupling reactions, or in case halogen atoms are required in the structure of the final product, the insertion of the metal catalyst into the carbon-halogen bond is not desired, as it usually leads to side reactions and associated material losses. Not all halogens are evenly sensitive for this dehalogenation side reaction. The risk for dehalogenation is particularly high with chlorine, bromine and iodine, and much lower with fluorine-containing substrates.

A variety of methods have therefore been attempted in order to increase the selectivity of metal catalysed reductive aminations of one functional group in the presence of one or more halogen atoms elsewhere in the substrate molecule, in particular for chlorine, bromine and iodine.

One method involves the addition of modifiers to the reaction mixture or working into alternative reaction media.

U.S. Pat. No. 5,011,996 for instance discloses in Example 14 a process for the reductive amination of ortho-chloro benzaldehyde with ammonia, in methanol, under 90 bar of nitrogen supplemented by hydrogen addition until completion of the hydrogen uptake. Methanol-moist Raney nickel was used as the catalyst and a small amount of bis-(2-hydroxyethyl) sulphide was added as a modifier. The reaction mixture contained 90.5% ortho-chloro-benzylamine as the prime product, together with 0.9% of benzylamine and 6.8% of ortho-chloro-benzyl alcohol.

U.S. Pat. No. 6,429,335 B1 discloses in Example 1 also a process for the reductive amination of ortho-chloro benzaldehyde with ammonia, now under 140 bar of hydrogen using Raney nickel or Raney cobalt, to produce the primary amine ortho-chlorobenzylamine. This process operates in the presence of an amount of disodium tetraborate decahydrate (borax), optionally together with a small amount of bis (hydroxyethyl) sulphide, and obtains a product selectivity of at most 95.87% wt. The main byproduct is 3.19% wt of ortho-chloro-benzyl alcohol, and only 0.1% wt of benzylamine was found.

WO 2014/135508 A1 and EP 2774911 A1 disclose a process for the production of ortho-chloro-N,N-dimethyl-benzylamine by the reaction of ortho-chloro-benzaldehyde (2-Cl-BZA) with dimethylamine (DMA), in the presence of acetic acid, hydrogen and a nickel catalyst. The examples use a molar ratio of DMA/2-Cl-BZA of at least 1.5/1, and demonstrate that a higher yield of the desired product is achieved when this molar ratio is increased further.

US 2007/0078282 A1 discloses reductive amination using bifunctional catalysts containing a hydrogen-active component with an acidic oxide as cocatalyst. Only example 4 starts from a halogen-containing substrate, the halogen being fluorine. Fluorine is however known to be particularly insensitive to dehalogenation, much less than the other common halogens.

Other chemical pathways to obtain particularly valuable polyfunctional products containing halogens have also been explored.

The stoichiometric alternative to the catalytic reductive amination of o-chloro benzaldehyde to obtain o-chloro-benzyl-dimethylamine is exemplified by WO 2013/017611 A1, which describes a process to obtain o-chloro-benzyl-dimethylamine from o-chloro-benzyl chloride and dimethylamine. The yield of the reaction was at most 95.4% of theory. The reaction was performed without involving any catalyst and a chloride salt was obtained as an undesired byproduct. Such processes based on stoichiometric chemistry in general suffer from poor atom efficiency and production of large amounts of waste.

There therefore remains a need for a highly selective conversion in the reductive amination of only the first functional group, on a substrate containing at least one further functional group containing a halogen atom. The desire is to achieve industrially acceptable reaction rates while keeping the further functional group containing the halogen atom substantially untouched and present in the reaction product.

It is an objective of the process according to the present invention to carry out the selected chemical reaction with a low degree of dehalogenation. Fluorine is known to be significantly less sensitive to dehalogenation than the heavier and more bulky halogens chlorine, bromine and/or iodine. A fluorine atom initially present in the feed substrate molecule therefore has a higher likelihood to remain present in the reaction product as compared to the other halogens. There therefore remains a particular need for a highly selective catalyst which will allow a low degree of dehalogenation in a substrate containing at least one further functional group containing chlorine, bromine and/or iodine.

The present invention aims to obviate or at least mitigate the above described problem and/or to provide improvements generally.

SUMMARY OF THE INVENTION

According to the invention, there is provided a process and a particularly useful composition which may be prepared using the process, as defined in any of the accompanying claims.

The invention therefore provides a process for performing a reductive amination of a first functional group in an organic feed substrate, which feed substrate comprises at least one further functional group containing a halogen atom, wherein the halogen atom is selected from the list consisting of chlorine, bromine, iodine and combinations thereof, in the presence of hydrogen and a heterogeneous catalyst comprising at least one first metal selected from the list consisting of palladium, Pd, platinum, Pt, rhodium, Rh, iridium, Ir, and ruthenium, Ru, and in absence of a catalytic amount of any second metal selected from the list consisting of silver, Ag, nickel, Ni, cobalt, Co, tin, Sn, bismuth, Bi, copper, Cu, gold, Au and combinations thereof, whereby the heterogeneous catalyst has been heat-treated prior to the reductive amination at a temperature in the range of 100-600° C. for a period of at least one hour, preferably at least two hours.

The applicants select the first metal from the list consisting of palladium, Pd, platinum, Pt, rhodium, Rh, iridium, Ir, and ruthenium, Ru. More preferably the applicants use palladium or platinum as the first metal. Palladium and platinum are more readily available than most of the other noble metals in the list of first metals, and are therefore more readily obtainable as a raw material, usually also at a lower cost for the production of the catalyst. Palladium and platinum are also metals which are easier to recover or to recuperate from a spent catalyst, and to recycle into a new use. Although palladium and platinum are typically not recognized as highly selective catalysts for performing reductive aminations of substrates containing halogens, we have found that the catalysts containing palladium or platinum as the first metal, and in absence of the second metal as specified above, when properly heat treated according to the present invention, surprisingly combine the benefits of a high activity with a greatly improved selectivity when reacting halogen containing substrates. Without wanting to be bound by this theory, the applicants believe that this surprising effect is related to a growth of the metal particles on the catalyst during the heat treatment. The applicants have at least found indicative evidence hereof by X-ray diffraction (XRD) analysis of catalysts before and after the heat treatment. The applicants believe that this effect and advantage extends also to the other first metals, as specified. Ruthenium may further be advantageous to use as a first metal, because it is also more readily available as compared to some other first metals. One advantage is that is usually also available at a somewhat lower cost.

Preferably, the applicants use a monometallic catalyst for the process according to the present invention, whereby is meant a catalyst comprising only catalytic amounts of the at least one first metal. We have also found that such a monometallic catalyst is easier to obtain as compared to bimetallic catalysts. Bimetallic catalysts, or catalysts with even more different metals, typically require at least two steps for depositing the metals on the catalyst. With bimetallic catalysts, or catalyst containing even more different metals, whereby the different metals should collaborate with each other in order to obtain the desired catalytic benefits, it is also usually more critical that the metals have the desired distribution over the support surface of the catalyst, and also that the deposits of the different metals are sufficiently close to each other to enable the catalytic cooperation between the two metals. The applicants have found that the catalysts containing only catalytic amounts of the first metals, whereby there is no cooperation between different metals required in order to obtain the desired effect, are easier to obtain as compared to the catalysts requiring the presence of also second metals in catalytic quantities in order to achieve the desired catalytic effects. Furthermore, such single metal or monometallic catalysts may often have a lower risk of metal leaching, and the metal may be more easily recovered and refined from the spent catalyst. Another advantage of monometallic catalysts over bimetallic catalysts is that they may be manufactured with a higher reproducibility.

We have found that the process according to the present invention is highly selective in performing the desired chemical conversion of the first functional group, while keeping the further functional group containing the halogen atom substantially intact such that the halogen remains present in the reaction product. We have for instance found that the dehalogenation of a halide function as the further functional group on the substrate, a side reaction which is occurring when using monometallic palladium catalyst, may be significantly suppressed, and essentially avoided, when using the process according to the present invention. The dehalogenated byproduct is typically useless, and possibly even a nuisance. The same may apply to the halide containing byproduct (e.g. HX) of the undesired dehalogenation reaction, which for instance may cause corrosion to the reactor or downstream processing equipment. The side reaction thus typically represents a downgrade of valuable starting materials, and adds additional burden for removal of the byproducts from the desired reaction product or for selecting more precious construction materials. The process according to the present invention thus brings the advantage of producing a highly pure desired reaction product, which requires much less clean-up, if any, before it may be put to further use. The process also brings the advantage of highly efficient use of the starting organic substrate, with very low downgrade, if any, to byproducts which may be useless or undesired in the prime reaction product, in which case the byproducts must be separated off and typically discarded or even require additional efforts for disposal in a responsible manner. Furthermore the process according to the present invention avoids the use of expensive and generally less active platinum as the metal in the catalyst without compromising the selectivity.

The applicants have found that the process according to the present invention may be particularly suitable for the reductive amination of ortho-chloro-benzaldehyde in the presence of dimethyl amine, DMA, to produce ortho-chloro benzyl dimethyl amine, o-CI-BDMA. The applicants have found that the process according to the present invention may produce the desired o-CI-BDMA, also known as ortho-CI-BDMA or 2-CI-BDMA, in very high yield and in particularly high purity, with very little byproducts.

The process according to the present invention therefore is able to provide a composition comprising, as measured by gas chromatography, GC,
a) at least 98.0% wt of o-chloro-benzyl-dimethylamine, o-CI-BDMA,
b) at most 0.40% wt of ortho-chloro toluene, preferably the total of all chloro toluene isomers, and
c) at least 0.005% wt or 50 ppm by weight of o-chloro-benzyl alcohol.

The content of o-chloro-benzyl alcohol in this composition may preferably be at least 0.007% wt of 2-chloro-benzyl alcohol, more preferably at least 0.009% wt, even more preferably at least 0.010% wt, yet more preferably at least 0.012% wt, preferably at least 0.015% wt, more preferably at least 0.020% wt, even more preferably at least 0.030% wt, preferably at least 0.040% wt, more preferably at least 0.05% wt, preferably at least 0.07% wt of 2-chloro-benzyl alcohol, more preferably at least 0.09% wt, even more preferably at least 0.10% wt, yet more preferably at least 0.12% wt, preferably at least 0.15% wt of 2-chloro-benzyl alcohol. Optionally the composition contains at most 1.0% wt of 2-chloro-benzyl alcohol.

The applicants have found that this composition is particularly suitable as an intermediate for the production of more complex structures in multi-step synthesis routes. Such routes may lead to agrochemical or pharmaceutical active ingredients. The applicants believe that the low presence in the composition of ortho-chloro toluene, more generally the total of all chloro toluenes, in particular of the mono chloro toluenes, and preferably also of chloro dichloromethyl benzenes, also known as chloro benzalchlorides, in particular of o-chloro dichloromethyl benzene, also known as 2-chloro benzyl dichloride or ortho-chloro benzalchloride, preferably below the detection limit in the most appropriate analytical technique, and more preferably the total absence thereof, makes the composition highly suitable for use as raw material in the further steps of many synthesis routes. The applicants have found that the compounds such as a chloro toluene, such as mono chloro toluene, and ortho-chloro dichloromethyl benzene, are contaminants which participate in downstream steps when the composition is used as an intermediate for the synthesis of complex chemical compounds. However, they do not lead to the desired compound and hence represent a loss of valuable reagents. The compounds which result from these contaminants are at best inert but may also exhibit effects which are undesired in the final composition, in which case an excessive occurrence of these side reactions creates a need for extra purification steps in the overall synthesis process.

The composition containing o-CI-BDMA is in particular useful if such further steps comprise metallation reactions such as lithiation or Grignard reactions, such as described in US 2010/0113778 A1, or coupling reactions such as the reactions known as the Heck, the Sonogashira, the Suzuki or the Stille coupling.

The applicants have found that a small amount of o-chloro-benzyl alcohol being present in the composition obtainable by the process according to the present invention, which may be present when the composition is obtained using the process according to the present invention, is of little consequence for the further use of the composition, such as in many further synthesis steps and/or many uses of the products thereof.

DETAILED DESCRIPTION

The present invention will be described in the following with respect to particular embodiments and with reference to certain drawings but the invention is not limited thereto but only by the claims. Any drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B. Accordingly, the terms "comprising" and "including" encompass the more restrictive terms "consisting essentially of" and "consisting of".

The terms "ortho", "meta" and "para", abbreviated by o-, m-, p-respectively, are used to indicate the relative position of two substituents on an aromatic cycle, as defined by the International Union of Pure and Applied Chemistry (IUPAC). Taking the standard priority rules for functional groups and substituents into account, their positioning may also be referred to by numbers in chemical nomenclature. In this respect, the indication 2-, 3-, and 4-correspond to o-, m-, and p-respectively.

In an embodiment, the current invention involves the use of a heat treated Pd catalyst for the reductive conversion of halogenated substrates in the presence of hydrogen, and in particular the reductive amination of such substrates. Being a catalytically very active metal, Pd has the advantage over Pt of being much cheaper and being easier to recover.

The process according to the present invention is performed in the presence of hydrogen. The use of hydrogen ($H_2$) as the reducing agent is much favoured by the presence of a metal catalyst. Such a catalyst is believed to be instrumental in activating the molecular hydrogen by weakening the H—H bond. Next to the activation of $H_2$, the catalyst may also play a role in other reaction steps, such as the other steps involved in the reductive amination mechanism. This role together with the characteristics of the reaction conditions (such as the presence of free amine, water, the typical temperature and pressure range, etc. . . . ) make that reductive amination catalysts are often tailored for this specific process, especially when sensitive (e.g. multifunctional) substrates are involved. It was therefore surprising to see that the heat treated catalyst as used in the process of this invention was found to show such good halogen retention properties.

Suitable organic feed substrates for the process according to the current invention are organic molecules containing at least one reducible functional group next to at least one halogen atom.

In an embodiment of the process according to the present invention, the first functional group is selected from the list consisting of an aldehyde, a ketone, and combinations thereof. Reducible functional groups which may suitably be hydrogenated with the heat treated Pd catalyst according to the process of the present invention are ketones, aldehydes, nitro groups, carboxylic acids, carboxylic esters, carboxylic amides, unsaturated carbon-carbon bonds, nitrile, imine and oxime groups. Such functional groups may be present in the substrate already when this is entered into the reactor, but may also be generated in situ during the course of a chemical reaction.

In an embodiment of the process according to the present invention, the first functional group in the feed substrate is first converted in situ by reaction with an additional reagent to form a reducible functional group. In particular, ketones and aldehydes may be converted to various intermediates, under the conditions of a reductive amination reaction, and which intermediates are subsequently hydrogenated with hydrogen to the final product of the reaction.

The halogen atom (X) is a selected element from group 17 in the IUPAC periodic table dated 22 Jun. 2007. In an embodiment of the process according to the present invention, the further functional group is selected from the list consisting of a chloride, a bromide and an iodide. The halogen is typically attached to the substrate by means of a covalent bond with a carbon atom (C—X bond). The carbon atom to which the halogen is attached may be either sp, $sp^2$ or $sp^3$ hybridized.

In an embodiment, the process according to the present invention is for the reductive amination of a halo-benzaldehyde in the presence of a nitrogen containing compound, preferably the nitrogen compound being selected from ammonia, a primary amine and a secondary amine, and mixtures thereof, preferably for the production of ortho-chloro benzyl dimethyl amine, o-CI-BDMA, by the reductive amination of ortho-chloro-benzaldehyde in the presence of dimethyl amine, DMA.

For a reductive amination, chloro benzaldehydes (ortho, meta or pare) are particular interesting substrates, as they may lead to the corresponding chloro benzylamines. Both the chloro and the amine functionality in these reaction products make the products of interest as further chemical building blocks, because the functionalities represent suitable points for further functionalization in subsequent synthesis steps. The chlorine atom offers opportunities for metallation reactions, such as lithiation or Grignard reactions, while the amine group offers possibilities for a further reductive amination or in case of a tertiary amine for quaternisation and conversion into other suitable leaving groups.

Reductive amination is the reaction well known in chemistry for the synthesis of primary, secondary or tertiary amines starting from a suitable ketone or aldehyde. The term "amination" relates to the reaction part in which an amine functionality is incorporated into the substrate. The term "reductive" relates to the observation, when comparing the feed substrate and the product of a reductive amination reaction, that a reduction has necessarily also taken place. In chemistry, a reduction reaction refers in general to the gain of electrons of an atom or a molecule. In organic chemistry, reductions are usually related with the disappearance of unsaturations, such as double bonds, from the substrate molecules. The net result of a reductive amination of a ketone or aldehyde is the conversion of a C=O double bond into a C—N single bond.

In an embodiment of the process according to the present invention, the reductive amination is performed in two steps, in the first step reacting the aldehyde with the nitrogen containing compound, and in the subsequent step introducing hydrogen and the catalyst, preferably the two steps being performed in the same reaction vessel. The general mechanism of reductive aminations is believed to start with the nucleophilic addition of ammonia or a primary or secondary amine species to the carbonyl group of the ketone or aldehyde. Such addition may occur with or without the aid of a catalyst. The resulting adduct, sometimes referred to as "hemiaminal", may react further by the elimination of water to the corresponding imine. The occurrence of imine formation is not essential for the outcome of the reductive amination, and in case of the use of secondary amines as reagents, this even is impossible. In this case, enamines may be formed as intermediates.

The next step in the mechanism of the reductive amination involves a reduction step. All three of an imine, a hemiaminal or an enamine may be the substrate before and on which the reduction is taking place. For this step, a reducing agent is required, which itself will be oxidized after the reaction has been effectuated. Such as for other hydrogenation reactions, stoichiometric reagents are sometimes used for this purpose, such as for instance formic acid or hydrides such as borohydrides or aluminum hydrides, but from the point of view of atom efficiency and process economics, the use of hydrogen gas is particularly favourable.

In an embodiment of the process according to the present invention, the heterogeneous catalyst comprises the first metal at a concentration in the range of 0.1-10.0% by weight, preferably at a concentration of at least 0.5% by weight, more preferably at least 1.0%, even more preferably at least 1.5%, yet more preferably at least 2.0%, preferably at least 2.5% by weight, more preferably at least 3.0%, even more preferably at least 3.5%, yet more preferably at least 4.0%, preferably at least 4.5% by weight, and optionally at a concentration of at most 10.0%, preferably at most 9.0%, more preferably at most 8.0% wt, even more preferably at most 7.0% wt, yet more preferably at most 6.0% wt, preferably at most 5.0%, more preferably at most 4.0%, all based on the total weight of the catalyst. The applicants have found that these levels provide an advantageous balance between catalyst performance and the costs and efforts associated with the production of the catalyst.

In an embodiment of the process according to the present invention, the heterogeneous catalyst comprises the second metal or combinations thereof at a concentration of at most 0.1% by weight, based on the total weight of the catalyst, preferably at most 0.05% by weight, more preferably at most 0.01% by weight, even more preferably at most 0.005% by weight.

In an embodiment, the process according to the present invention further comprises the step of putting the first metal onto a support by precipitation. The applicants have found that the precipitation method is a very convenient method for putting a metal such as palladium onto a support. Suitable precipitation methods for putting palladium metal onto a support are well known in the art.

In an embodiment of the process according to the present invention, the chemical conversion selected from reductive amination, and/or the catalyst heat treatment step, is performed in the presence of a solvent, preferably an organic solvent, preferably the solvent comprising at least one alkanol, preferably methanol, preferably the solvent being present in a weight ratio relative to the organic feed substrate in the range of 0.1-20 g/g, preferably at least 0.2 g/g, more preferably at least 0.3 g/g, optionally at most 15.0 g/g, preferably at most 10.0 g/g, more preferably at most 5.0 g/g, even more preferably at most 4.0 g/g, yet more preferably at most 3.0 g/g, preferably at most 2.0 g/g, even more preferably at most 1.0 g/g. Reductive amination reaction and/or the heat treatment step, according to the process of the present invention may occur in any suitable medium. Solvents such as water, alcohols (e.g. methanol), tetrahydrofurane (THF), dioxane, alkanes may be used advantageously. A solvent may bring advantages to such reductive amination reaction, such as an improved hydrogen solubility, a decreased viscosity of the reaction mixture, an improved mixing efficiency, an improved heat transfer, etc. . . . The concentration of the substrate and products in such solvents may be between 1 and 50%, preferably between 5 and 40%, more preferably between 10 and 40% by weight, based on the total reaction mixture. Highly diluted reaction mixtures may result in poor space-time yields, while in case of highly concentrated reaction mixtures, the benefits of the solvent may be minimized. In case the reaction substrates and products are liquids under the reaction conditions applied, the reaction may be performed without the addition of a solvent. One may also choose to add small amounts of solvents to the reaction mixture, e.g. 1 to 50%, preferably 5 to 40%, more preferably 10 to 30% by weight, relative to the total reaction mixture. Such addition may have particular advantages such as to improve the catalyst performance, to decrease the autogenous pressure of the reaction mixture, to prevent phase separation to occur, etc. . . .

In case of the reductive amination of o-chloro benzaldehyde with dimethyl amine (DMA), we have found that the addition of small amounts of methanol to the reaction mixture improves the yield and operability of the process significantly. Without wanting to be bound by this theory, the methanol is believed to increase the solubility of the highly volatile amine and therefore enhancing the reaction rate in the liquid phase. Additionally, the presence of methanol may possibly prevent the occurrence of two separate liquid phases during the reductive amination, possible because of any liberation of water as the co-product in the reaction.

In an embodiment of the process according to the present invention, the heterogeneous catalyst has been heat treated, such as prior to its use in the process, at a temperature in the range of at least 200° C., preferably at a temperature of at least 250° C., more preferably at least 300° C., even more preferably at least 350° C., yet more preferably at least 400° C., and optionally at a temperature of at most 550° C., preferably at most 500° C., even more preferably at most 450° C., preferably the heat treatment being performed for at least 1 hour, preferably 2 hours, more preferably at least 3 hours, even more preferably at least 4 hours, yet more preferably at least 5 hours, preferably at least 6 hours, more preferably at least 7 hours, even more preferably at least 8 hours, and for at most 24 hours, preferably at most 18 hours, more preferably at most 12 hours, even more preferably at most 10 hours, yet more preferably at most 8 hours, preferably at most 6 hours, more preferably at most 5 hours, even more preferably at most 4 hours, yet more preferably at most 3 hours. The applicants prefer to heat-treat the catalyst at about 400° C., in nitrogen, for a period of about 2 hours with a $N_2$ flow at a velocity expressed as weight/weight/hour (WWH) of about 0.225-0.250 per hour ($h^{-1}$), and this after first having dried the catalyst at about 80° C. for a period of 3 hours, in stagnant air or preferably under a flow of gas to remove water vapour, i.e. until no substantial further weight loss of the catalyst being dried could anymore be noticed.

In an embodiment of the process according to the present invention, the atmosphere during the heat treatment is a gaseous atmosphere, more preferably selected from the list consisting of hydrogen $H_2$, nitrogen $N_2$, an inert gas and air.

In an embodiment of the process according to the present invention, the heat treatment of the heterogeneous catalyst has been performed by exposure to a flow of gas at a WWH in the range of from 0.0200 to 2.0000 $h^{-1}$, preferably at least 0.0375 $h^{-1}$, more preferably at least 0.050 $h^{-1}$, even more preferably at least 0.075 $h^{-1}$, yet more preferably at least 0.120 $h^{-1}$, preferably at least 0.150 $h^{-1}$, more preferably at least 0.200 $h^{-1}$, even more preferably at least 0.220 $h^{-1}$, and optionally at most 1.500 $h^{-1}$, preferably at most 1.000 $h^{-1}$, more preferably at most 0.500 $h^{-1}$, even more preferably at most 0.300 $h^{-1}$. The applicants have found that the heat-treatment under these conditions is particularly convenient but also particularly effective in obtaining the technical effects which are the target of the present invention.

In an embodiment of the process according to the present invention, the heterogeneous catalyst at the start of the heat-treatment contained at most 10% wt of free water, preferably at most 8% wt of free water, more preferably at most 5% wt of free water, preferably at most 3.0% wt of free water, more preferably at most 2.0% wt of free water, even more preferably at most 1.0% wt of free water, and optionally at least 0.01 wt % free water. The applicants have found that this feature reduces the risk that the heterogeneous catalyst becomes damaged during the heat-treatment step. Free water is defined in this context as the water which may be removed by drying at a temperature of at most 100° C., as observed by weight loss.

In an embodiment of the process according to the present invention, the heterogeneous catalyst has been dried prior to the heat-treatment. The applicants have found that a drying step is a very convenient step in order to achieve a limited free water content of the heterogeneous catalyst, which was found to bring the advantage of reducing the risk that the heterogeneous catalyst becomes damaged during the heat-treatment step. A drying step is defined in this context as an heating of the catalyst to a temperature of less than 100° C. for a period of time suitable for removing the desired amount of free water, as measurable by weight loss. The drying step may be performed using a heated gas flow to remove vaporising water. The drying step may be performed separate from the heat treatment step, or may be performed during the starting phase of the heat treatment step, for instance by keeping the catalyst under a gas flow at the prescribed temperature for a suitable time before the temperature is raised for starting the heat treatment. The applicants have found that this last combination of drying step and heat treatment step is particularly convenient for implementation at a commercial scale.

In an embodiment of the process according to the present invention, the heat treatment is made in the presence of a substrate or a solvent. Preferably the substrate is in the liquid form. The applicants have found that the use of a liquid during the heat treatment is a very convenient way to bring heat energy into the heterogeneous catalyst which is solid. The applicants have found that transferring heat to a solid by use of a liquid is much more effective than by using only a gaseous carrier for introducing the heat energy.

In an embodiment of the process according to the present invention, the heterogeneous catalyst has a support selected from the list consisting of carbon, alumina, silica, zeolite, clay, porous polymer and hybrid polymer, preferably a carbon support, more preferably an activated carbon, even more preferably an activated carbon which has been activated by a treatment with an acid. The applicants have found that the heterogeneous catalyst on a carbon support is particularly sensitive to the heat treatment according to the present invention, and that such catalyst is particularly effective in obtaining the desired effect of the present invention.

For the ease of handling, the catalyst is preferably supported on a solid carrier. A suitable carrier for the support of the metals in the catalyst of the process according to the present invention is activated carbon, because of its large specific surface area and its good adhesion properties. Further treatment, such as steaming, acid washing, sulphonation, or the like, may be given to the support, because this often enhances the adsorption properties of the activated carbon. Other carbon carriers such as graphite or carbon nanotubes (CNT) may be used as the support of the catalyst. Carbon supports offer the additional advantage that the process for recycling the metal or metals, at the end of life of the catalyst, is much simplified as compared with other supports.

Other types of materials known by people skilled in the art may suitably be used as the catalyst support: alumina, silica, zeolite, clay, porous polymer and hybrid polymer, and combinations thereof.

The total metal loading on the catalyst support may be in the range of 0.1 to 40% by weight, more preferably at least 0.2%, more preferably 0.5%, more preferably at least 1.0%, even more preferably at least 2.0%, yet more preferably at least 3.0%, more preferably at least 4.0%, even more preferably at least 5.0%, and optionally at most 35% by weight, preferably at most 30%, more preferably at most 25.0%, even more preferably at most 20.0%, yet more preferably at most 15.0%, preferably at most 10.0%, more preferably at most 7.5%, even more preferably at most 5.0%, whereby the levels are expressed relative to the total weight of the catalyst.

The supported catalyst may occur in a form which is most suitable and desired for the process, such as a powder, in the form of a granule, an extrudate, or combinations thereof. With a powder catalyst, the catalyst may after use be separated from the reaction mixture by filtration. With granules and/or extrudates, the catalyst and the reaction mixture may be separated from each other by simple draining of the reactor vessel containing the catalyst, which may for instance be arranged in a fixed bed arrangement.

In an embodiment of the process according to the present invention, the heterogeneous catalyst has a metal area, as measured by carbon monoxide chemisorption of at least 0.5 $m^2/g$, preferably at least 1.0 $m^2/g$, more preferably at least 2.0 $m^2/g$, even more preferably at least 3.0 $m^2/g$, yet more preferably at least 4.0 $m^2/g$, optionally at most 12.0 $m^2/g$.

In an embodiment of the process according to the present invention, the heterogeneous catalyst has an average metal particle size in the range of 2 to 20 nm, preferably at least 2.0 nm, more preferably at least 3.0 nm, even more preferably 4.0 nm, optionally at most 20.0 nm, preferably at most 15.0 nm, more preferably at most 12.0 nm, even more preferably at most 10.0 nm, yet more preferably at most 9.0 nm or even at most 8.0 nm. The average metal particle size is preferably measured using X-ray powder diffraction (XRPD), whereby the applicants prefer to use the Sherrer equation based on half-peak width.

In an embodiment of the process according to the present invention, the heterogeneous catalyst has been pre-reduced prior to the step of contacting the catalyst with the organic feed substrate, preferably by subjecting the catalyst at a temperature of at least 120° C., preferably at least 140° C. to a hydrogen atmosphere of at least 5 bar gauge, preferably at least 8 bar gauge during a period of at least 30 minutes, preferably at least 45 minutes, preferably the pre-reduction being performed with the catalyst being in contact with an organic liquid phase, preferably an alkanol, more preferably methanol. The applicants prefer to perform this pre-reduction step with the catalyst in contact with methanol, at a temperature of about 150° C., and under a hydrogen partial pressure of about 10-11 bar absolute, and this for a period of about three hours. Alternatively, the applicants may perform the pre-reduction step with the catalyst in contact with methanol at a temperature of about 180° C., and under a hydrogen partial pressure of about 10-11 bar absolute, and this for a period of about one hour. The applicants have found that this pre-reduction step allows the catalyst to exhibit its desired advantageous performance from very early on after starting the process.

In an embodiment of the process according to the present invention, at least 80% of the feed substrate is retaining the at least one further functional group after the conversion, preferably at least 85%, more preferably at least 90%, even more preferably at least 95%, preferably at least 97%, more preferably at least 98%, even more preferably at least 99.0%, preferably at least 99.4%, more preferably at least 99.5%, even more preferably at least 99.6% of the feed substrate is retaining the at least one further functional group after the conversion. The applicants have found that these results are readily achievable with the catalyst of the process according to the present invention.

In an embodiment of the process according to the present invention, the reductive amination is performed at a $H_2$ partial pressure in the range of 0.01-250 bar gauge, preferably at least 0.1, more preferably at least 1, even more preferably at least 5.0 bar gauge, even more preferably at least 10.0 bar gauge, yet more preferably at least 20 bar gauge, preferably at least 30 bar gauge, more preferably at least 40 bar gauge, even more preferably at least 50 bar gauge, and optionally at most 200 bar gauge, preferably at most 150 bar gauge, more preferably at most 100 bar gauge, even more preferably at most 80, yet more preferably 70, and preferably at most 60 bar gauge.

In an embodiment of the process according to the present invention, the reductive amination is performed at a temperature in the range of 0-300° C., preferably at least 10° C., more preferably at least 20° C., even more preferably at least 30° C., yet more preferably at least 40° C., preferably at least 60° C., more preferably at least 80° C., and even more preferably at least 90° C., and optionally at most 250° C., preferably at most 200° C., more preferably at most 180° C., even more preferably at most 150° C., yet more preferably at most 130° C., preferably at most 120° C., more preferably at most 110° C., even more preferably at most 100° C.

In an embodiment, the process according to the present invention is performed in continuous mode. The applicants have found that the catalyst itself, as well as its performance, may be arranged to be fairly stable over time, such that the process is highly suitable for a continuous operating mode. This brings significant advantages in terms of production rate, volumetric efficiency of the process equipment, control equipment, steadiness of performance, operator attention and intervention frequency, automation capabilities, many of which represent significant advantages to the process owner.

The applicants have found that the process according to the present invention may also be performed in batch mode. The applicants have found that the catalyst, upon separation from the reaction medium after a first performance of the process, may readily be reused in a second performance of the process, preferably without any intermediate treatment. The applicants have found that at least 5, preferably at least 10, and more preferably at least 15 reuse cycles may be performed with the same catalyst in the process according to the present invention. The applicants have found that some metal may leach from the catalyst during the early performances of a fresh catalyst in the process according to the present invention, but that such metal leaching is at a level which is substantially insignificant in terms of amount of metal lost from the catalyst, and also does not cause any substantial loss of performance of the catalyst.

In an embodiment, the process according to the present invention further comprises the purification of the converted substrate, preferably by the distillation of the reaction product, for reducing the content of at least one compound selected from a reaction byproduct, a feed impurity, a solvent, and unreacted feed substrate.

In an embodiment wherein the process according to the present invention is used for the production of ortho-chloro benzyl dimethyl amine, 2-CI-BDMA, the process is further comprising subjecting the 2-CI-BDMA to a Grignard reaction, comprising for example in a first step the preparation of a Grignard reagent in which a magnesium atom is introduced in between the benzene ring and the chlorine atom, followed by a second step wherein the Grignard reagent is reacted with an oxalic acid dialkyl ester.

In an embodiment wherein the process according to the present invention is used for the production of ortho-chloro benzyl dimethyl amine, 2-CI-BDMA, the process is further comprising the conversion of 2-CI-BDMA into o-chloromethylphenylglyoxylic esters by a method such as described in US 2010/113778 A1. o-Chloromethylphenylglyoxylic esters are important intermediates for preparing agrochemically active compounds or microbicides of the methoximinophenylglyoxylic ester series. More particularly, US 2010/113778 A1 describes the production of strobilurines, a type of fungicides that are stated to inhibit the respiratory system of the fungi, and of which Kresoxim-methyl and Dimoxystrobin are named and exemplified as particularly interesting family members. In a further embodiment therefore, the process according to the present invention further comprises the production of a fungicide containing a methoximinophenylglyoxylic ester derivatived from 2-CI-BDMA, in particular derived from the composition according to the present invention.

In an embodiment wherein the process according to the present invention is used for the production of ortho-chloro benzyl dimethyl amine, 2-CI-BDMA, the process is further including the step of treating a surface with the fungicide containing the methoximinophenylglyoxylic ester which was derived from the 2-CI-BDMA obtained with the reductive amination. Such a surface may be from, but is not limited thereto, an agricultural field, an orchard, a leaf or stem of an agricultural crop, a slab, a floor tile, a façade, a wall or a roof of a building, a cardboard box or any other kind of packaging material, a portion of human skin, of human mucosa, of animal skin, or of animal mucosa. The fungicide composition may be a solid, such as a powder, or a liquid, in which the ester may be dissolved or dispersed in a carrier or solvent. The step of using the fungicide composition may be performed using any one of the methods known in the art, and combinations thereof, such as by spraying, by brushing, by pouring, by dusting, by mixing and the like, including combinations thereof.

In an embodiment of the composition produced by the process according to the present invention, the composition comprises at least 98.5% wt of 2-chloro-benzyl-dimethylamine, preferably at least 99.0% wt, more preferably at least 99.1% wt, even more preferably at least 99.2% wt, yet more preferably at least 99.3% wt of 2-chloro-benzyl-dimethylamine. The higher the content in 2-chloro-benzyl-dimethylamine, the more advantageously the composition may be applied in its desired application, such as a conversion to a further chemical derivative.

In an embodiment, the composition produced by the process according to the present invention comprises at most 0.04% wt of 2-chloro-dichloromethyl benzene, preferably at most 0.030% wt, more preferably at most 0.020% wt, even more preferably at most 0.015% wt, preferably at most 0.010% wt, more preferably at most 50 ppm by weight, even more preferably at most 10 ppm, of 2-chloro-dichloromethyl benzene. This component may represent an additional burden in applying the composition, such as generating corrosive components in subsequent reactions, and/or leading to undesired byproducts in subsequent conversions. The lower the content of 2-chloro-benzylchloride, the more advantageously the composition may be applied in its desired application, such as a conversion to a further chemical derivative.

In an embodiment, the composition produced by the process according to the present invention comprises at least 0.07% wt of 2-chloro-benzyl alcohol, preferably at least 0.09% wt, more preferably at least 0.10% wt. even more preferably at least 0.12% wt, yet more preferably at least 0.15% wt of 2-chloro-benzyl alcohol.

In an embodiment, the composition produced by the process according to the present invention comprises at most 1.0% wt of 2-chloro-benzyl alcohol, preferably at most 0.80% wt, more preferably at most 0.60% wt, even more preferably at most 0.50% wt, yet more preferably at most 0.40% wt of 2-chloro-benzyl alcohol.

The applicants have found that the 2-chloro-benzyl alcohol may acceptably be present in the composition without jeopardising or affecting the performance of the composition in many of its applications, such as particular conversions into further chemical derivatives, in particular those conversions and uses which have been described in more detail elsewhere in this document. The applicants have found that there is for many of such applications little to no need for the removal of any 2-chloro-benzyl alcohol which may be present in the composition, in particular not when it is present at the levels as specified. This represents an advantage because the removal of 2-chloro-benzyl alcohol from the prime product 2-chloro-benzyl-dimethylamine, and this to very low levels, may bring significant additional complexity to the process.

In an embodiment, the composition produced by the process according to the present invention comprises at most 0.20% wt of 2-chloro-benzaldehyde, preferably at most 0.15% wt, more preferably at most 0.10% wt, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC, if needed assisted by mass-spectrometry. This 2-chloro-benzaldehyde does not contribute to many of the applications of the composition. A presence at a lower level of this component therefore represents an improved effectiveness and brings improved efficiencies in the further use and application of the composition.

In an embodiment, the composition produced by the process according to the present invention comprises at most 0.40% wt of 4-chloro-benzyl dimethylamine, preferably at most 0.30% wt, more preferably at most 0.20% wt, even more preferably at most 0.10% wt of 4-chloro-benzyl dimethylamine, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. The applicants have found that this component may represent an additional burden in applying the composition, such as in subsequent reactions, and/or may lead to undesired byproducts in subsequent conversions which in addition may be rather difficult to separate from the desired product of such conversion. The lower the content of 4-chloro-benzyl dimethylamine, the more advantageously the composition may be applied in its desired application, such as a conversion to a further chemical derivative.

In an embodiment, the composition produced by the process according to the present invention comprises at most 0.35% wt of ortho-chloro toluene, preferably at most 0.30% wt, more preferably at most 0.20% wt. even more preferably at most 0.10% wt of ortho-chloro toluene, preferably at most 0.05% wt, more preferably at most 0.03% wt, even more preferably at most 0.01% wt, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. Preferably the specified levels apply to the total of all chloro toluene isomers together. The applicants have found that this component, and also its isomers, may represent an additional burden in applying the composition, such as in subsequent reactions, and/or may lead to undesired byproducts in subsequent conversions which in addition may be rather difficult to separate from the desired product of such conversion. The lower the content of chloro toluenes, in particular of ortho-chloro toluene, the more advantageously the composition may be applied in its desired application, such as a conversion to a further chemical derivative.

In an embodiment, the composition produced by the process according to the present invention comprises at most 0.40% wt of benzyl dimethyl amine, preferably at most 0.30% wt, more preferably at most 0.20% wt, even more preferably at most 0.10% wt of benzyl dimethyl amine, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. This benzyl dimethyl amine does not contribute to many of the applications of the composition. A presence at a lower level of this component therefore represents an improved effectiveness and brings improved efficiencies in the further use and application of the composition.

In an embodiment, the composition produced by the process according to the present invention comprises at most 0.40% wt of 2-dimethylaminobenzyl dimethylamine, preferably at most 0.30% wt, more preferably at most 0.20% wt, even more preferably at most 0.10% wt of 2-dimethylaminobenzyl dimethylamine, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. This 2-dimethylamino-benzyldimethylamine does not contribute to many of the applications of the composition. A presence at a lower level of this component therefore represents an improved effectiveness and brings improved efficiencies in the further use and application of the composition.

In an embodiment, the composition produced by the process according to the present invention comprises at most 0.40% wt of benzaldehyde, preferably at most 0.30% wt, more preferably at most 0.20% wt, even more preferably at most 0.10% wt of benzaldehyde, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. This benzaldehyde does not contribute to many of the applications of the composition. A presence at a lower level of this component therefore represents an improved effectiveness and brings improved efficiencies in the further use and application of the composition.

The applicants have found that the process according to the present invention is particularly suitable, because the process is able to provide a high reaction rate and conversion to the desired 2-chloro-benzyl-dimethylamine, which achieves low levels of the unconverted feed substrate 2-chloro-benzaldehyde, and thanks to the high selectivity of the catalyst as specified, with low presence of less desired byproducts, such as 2-chloro-benzyl alcohol and/or benzyl dimethyl amine and/or 2-dimethylamino-benzyldimethylamine. In addition, the process according to the present invention for the production of 2-chloro-benzyl-dimethylamine has little to no presence of the other undesired components 2-chloro-benzylchloride and/or 4-chloro-dimethylbenzylamine and/or chloro toluene isomers, in particular ortho-chloro toluene. The composition obtainable by the process according to the present invention is thus particularly suitable for use in many of its applications, such as particular conversions into further chemical derivatives, in particular those conversions and uses which have been described in more detail elsewhere in this document.

Analyticals

For analysing the composition produced by the process according to the present invention, as well as in the monitoring of the process according to the present invention, the applicants prefer to use the following gas chromatography, GC, analytical method.

The GC apparatus is preferably an Agilent 6890N with split injector and a flame ionization detector (FID). The apparatus is equipped with a capillary column coated with a stationary phase type CP-Sil 5 CB with dimensions 60 m×320 μm×5.0 μm. The applicants prefer to use an injector temperature of 280° C., an injector volume of 1 μliter and a split ratio of 1/30. The applicants prefer to use helium as the carrier gas, with a flow of 2 ml/min at constant flow. The oven is given a temperature program of holding for 3 minutes at 60° C., and subsequently ramping up the temperature at a rate of 20° C. per minute up to 290° C., at which temperature the column is kept for an additional 15 minutes. The FID detector is kept at 300° C., and fed with a hydrogen flow of 45 ml/min and an air flow of 450 ml/min. Make up gas, preferably nitrogen, and column flow together are set at a total of 45 ml/min.

The applicants have found that the following components may readily be identified by specific retention peaks: methanol, DMA, TMA, ethylbenzene, benzaldehyde, benzyl dimethyl amine, ortho-chloro benzaldehyde, ortho-chloro benzylalcohol, ortho-chloro benzyl dimethyl amine, para-chloro benzyl dimethyl amine, ortho (dimethylamino) benzyl dimethyl amine. The applicants have further found that this GC technique may readily be assisted with the addition of mass-spectrometry, such as for determining concentrations in the lower levels down to 1 ppm wt or even below.

Depending on the sample, the sample may be diluted up to 10 times in isopropanol. Preferably 1% of the internal standard is added, upon which the sample is preferably vigorously mixed for at least one minute, and after which 1 μl of sample may be injected into the gas chromatograph.

EXAMPLES

Example 1: Preparation of Pd Catalysts

A 5% wt palladium catalyst having activated carbon (AC) as its support, commercially available under the reference E196NN/W 5%, was obtained from the company Evonik. An amount of 10 g of this catalyst was dried at 80° C. in static air for 3 hours and subsequently heat-treated under a nitrogen flow of either 10 ml/min or 30 ml/min, which respectively correspond to a WWH of 0.08 h$^{-1}$ and 0.25 h$^{-1}$, at the temperatures as specified below during a heat-treatment time of either 2 or 4 hours. Various different combinations of heat-treatment temperature, nitrogen flows and heat-treatment time parameters were tested in order to determine the effect of these parameters on the performance of the heat-treated catalyst.

Example 2: Preparation of Pt Catalysts

A 5% wt platinum catalyst having activated carbon as its support, commercially available under the reference F 1015 RE/W 5%, was obtained from the company Evonik. An amount of 10 g of this catalyst was dried at 80° C. in static air for 3 hours and subsequently heat-treated under a nitrogen flow of either 10 ml/min or 30 ml/min, which respectively correspond to a WWH of 0.075 h$^{-1}$ and 0.225 h$^{-1}$, at a temperature of 400° C. during a heat-treatment time of 2 hours. In addition, a Pt catalyst was tested having the same properties but having $Al_2O_3$ as the support. This 5% wt Pt on alumina was a commercial catalyst, obtained as such from the company Sigma Aldrich. Various different combinations of the nitrogen flows and other parameters were tested on these Pt-based catalysts, in order to determine the effect of these heat treatment parameters on the performance of the heat-treated catalyst.

Example 3: Reductive Amination of 2-chloro-benzaldehyde with DMA to Produce 2-Cl-BDMA In each experiment, a 100 mL autoclave (Parr) was loaded with 2.5 g of 2-chloro benzaldehyde (2-Cl-BZA) obtained from the company Sigma Aldrich and 12 ml of dimethyl amine in methanol solution having a concentration of 2 mole per liter (2M or 2 Molar). The reactor was sealed and the gas phase was flushed three times with nitrogen and then pressurized at 5 bar by the addition of nitrogen gas. The reactor was heated at 80° C. and then continuously stirred for 60 minutes at a temperature of 80° C. and a pressure of 5 bar. Then, the reactor was cooled to 30° C. and degassed. 8 mg of the catalyst obtained from Example 1 or Example 2 was added to the autoclave. The autoclave was heated in 15 minutes to 100° C. and hydrogen was added to a final pressure of 40 bar. The reductive amination reaction was allowed to proceed for the indicated time at 100° C. Then the reactor was cooled down and degassed at room temperature. Subsequently, a sample of the reaction product liquid was taken and analysed by gas chromatography (GC) and inductively coupled plasma spectroscopy (ICP). In one experiment, the catalyst was filtered and recycled in a repeat experiment in a second run under the same conditions.

The results obtained were reported in Tables 1 to 6. They are all expressed as selectivity (%), and hence are excluding any water, methanol, residual dimethylamine or 2-Cl-BZA which might still have been present in the reaction product samples.

Table 1 reports the results obtained using the palladium catalysts obtained from Example 1, primarily for different heat-treatment temperatures. The selectivity of the reaction for the catalysts which were heat-treated at 100° C. or 200° C. during only 2 hours is moderately improved compared to the selectivity of the reaction for the untreated catalyst. A much higher selectivity and yield may be observed for the catalyst which was heat-treated at the higher temperature of 400° C. In addition, the high selectivity brings the advantage of simplifying the product separation downstream of the reaction.

TABLE 1

| Catalyst and heat-treatment details | Reaction time (min) | Conv (%) | BDMA (%) | 2-Cl-BDMA (%) | 2-DMA-BDMA (%) | 2-Cl-BOH (%) | Others (%) |
|---|---|---|---|---|---|---|---|
| 5% Pd/AC untreated | 15 | 99.9 | 45.8 | 33.4 | — | 0.1 | 20.7 |
| 5% Pd/AC N2, 100° C., 2 h, 30 ml/min | 15 | 99.5 | 45.3 | 35.2 | — | 0.2 | 19.3 |
| 5% Pd/AC N2, 200° C., 2 h, 30 ml/min | 15 | 94.3 | 42.4 | 39.3 | — | 0.3 | 18.0 |
| 5% Pd/AC N2, 400° C., 2 h, 30 ml/min | 15 | 44.0 | 2.1 | 97.8 | — | — | — |
| | 30 | 82.3 | 2.4 | 96.2 | — | 1.1 | <0.5 |

Table 2 shows the beneficial effect of a higher nitrogen flow for the palladium catalyst as prepared in Example 1, heat-treated under different nitrogen flows. A high nitrogen flow of 30 ml/min during the heat-treatment step significantly improved the selectivity of the reductive amination both for 15 min and for 30 min reaction time, as compared to those for a nitrogen flow of 10 ml/min.

TABLE 2

| Catalyst and heat-treatment details | Reaction time (min) | Conv (%) | BDMA (%) | 2-Cl-BDMA (%) | 2-DMA-BDMA (%) | 2-Cl-BOH (%) | Others (%) |
|---|---|---|---|---|---|---|---|
| 5% Pd/AC N2, 100° C., 2 h, 10 ml/min | 15 | 65.7 | 22.1 | 67.8 | — | — | 10.1 |
| | 30 | 89.6 | 23.5 | 66.8 | — | 0.5 | 9.2 |
| 5% Pd/AC N2, 400° C., 2 h, 30 ml/min | 15 | 44.0 | 2.1 | 97.8 | — | — | — |
| | 30 | 82.3 | 2.4 | 96.2 | — | 1.1 | <0.5 |

Table 3 shows the effects of heat-treatment time on the palladium catalysts from Example 1, heat-treated at the high temperature of 400° C. during either 2 hours or 4 hours, and this under a nitrogen flow of either 10 ml/min or 30 ml/min. Compared to the performance of the untreated catalyst, shown in Table 1, the selectivities obtained with heat-treated palladium catalysts are more favourable for all the examples listed in Table 3. Even the lower heat-treatment time at the low WWH (10 ml/min) already significantly improved the selectivity compared to untreated catalyst, albeit at the expense of some loss in conversion. The conversion loss was demonstrated to be readily recoverable by extending the reaction time, and this while the selectivity remained practically constant. Intensifying the heat-treatment by using a higher WWH of about 0.25 h$^{-1}$ (30 ml/min) significantly increased selectivity. Any penalty suffered on conversion by this change may readily be recovered by extending the reaction time. The best performing catalyst is the one that has been heat-treated for a longer time and at a higher WWH (30 ml/min). This particular catalyst combines a very high activity with a high selectivity, and hence results in a high yield.

TABLE 3

| Catalyst and heat-treatment details | Reaction time (min) | Conv (%) | BDMA (%) | 2-Cl-BDMA (%) | 2-DMA-BDMA (%) | 2-Cl-BOH (%) | Others (%) |
|---|---|---|---|---|---|---|---|
| 5% Pd/AC N2, 400° C., 2 h, 10 ml/min | 15 | 65.7 | 22.1 | 67.8 | — | — | 10.1 |
| | 30 | 89.6 | 23.5 | 66.8 | — | 0.5 | 9.2 |
| 5% Pd/AC N2, 400° C., 2 h, 30 ml/min | 15 | 44.0 | 2.1 | 97.8 | — | — | — |
| | 30 | 82.3 | 2.4 | 96.2 | — | 1.1 | <0.5 |
| Pd/AC N2, 400° C., 4 h, 30 ml/min | 15 | 99.4 | 5.9 | 93.7 | — | 0.6 | — |

The palladium catalyst which had been heat-treated at 400° C. for 2 hours under a 30 ml/min nitrogen flow, was recycled once in order to compare its performance in a second run with its performance in the first run. The results are shown in Table 4. The performance in the second run remained very comparable to this in the first run.

TABLE 4

| Run | Reaction time (min) | Conv (%) | BDMA (%) | 2-Cl-BDMA (%) | 2-DMA-BDMA (%) | 2-Cl-BOH (%) | Others (%) |
|---|---|---|---|---|---|---|---|
| 1 | 30 | 82.3 | 2.4 | 96.2 | — | 1.1 | <0.5 |
| 2 | 30 | 80.4 | 3.1 | 95.6 | — | 1.2 | — |

Tables 5 and 6 report results obtained with the platinum catalysts from Example 2.

Table 5 shows the effect of a higher nitrogen flow on the platinum catalysts from Example 2, heat-treated during 2 hours, under nitrogen flows of either 10 ml/min or 30 ml/min. Also for the platinum catalyst, any of the heat-treatments improves both the activity and the selectivity, regardless of what the nitrogen flow was.

TABLE 5

| Catalyst and heat-treatment details | Reaction time (min) | Conv (%) | BDMA (%) | 2-Cl-BDMA (%) | 2-DMA-BDMA (%) | 2-Cl-BOH (%) | Others (%) |
|---|---|---|---|---|---|---|---|
| 5% Pt/AC untreated | 15 | 87.9 | — | 88.1 | — | 4.2 | 6.7 |
| 5% Pt/AC N2, 400° C., 2 h, 10 ml/min | 15 | 88.3 | — | 94.8 | — | 4.6 | 0.2 |
| 5% Pt/AC N2, 400° C., 2 h, 30 ml/min | 15 | 99.9 | — | 96.5 | — | 3.1 | 0.2 |

Table 6 shows the results obtained with platinum catalysts supported on Alumina ($Al_2O_3$), untreated or heat-treated at 400° C. for 2 hours under a nitrogen flow of either 10 ml/min or 30 ml/min. Also for the platinum on aluminium oxide catalyst, the heat-treatment is demonstrated to improve the yield of the reaction; i.e. there is found a better performance in the combination of activity and selectivity, and thus a lower dehalogenation. In both cases, a longer reaction time pushes the conversion, while the selectivity of the reaction hardly changes. The effects of the present invention are thus proven to be also achievable with a support which is different from the activated carbon (AC) in the other examples.

TABLE 6

| Catalyst and heat-treatment details | Reaction time (min) | Conv (%) | BDMA (%) | 2-Cl-BDMA (%) | 2-DMA-BDMA (%) | 2-Cl-BOH (%) | Others (%) |
|---|---|---|---|---|---|---|---|
| 5% Pt/Al2O3 untreated | 15 | 71.1 | — | 58.5 | — | 39.1 | 1.6 |
|  | 30 | 86.9 | — | 61.5 | — | 36.8 | 1.4 |
| 5% Pt/Al2O3 N2, 400° C., 2 h, 10 ml/min | 15 | 69.3 | — | 65.4 | — | 30.2 | — |
|  | 30 | 92.8 | — | 64.5 | — | 28.3 | 1.1 |

Legend:
Conv          Conversion
2-Cl-BZA      2-chloro-benzaldehyde
BDMA          Benzyl dimethylamine
2Cl-BDMA      2-chlorobenzyl dimethylamine
DMA-BDMA      2-dimethylaminobenzyl dimethylamine
2-Cl-BOH      2-chlorobenzyl alcohol

Having now fully described this invention, it will be appreciated by those skilled in the art that the invention can be performed within a wide range of parameters within what is claimed, without departing from the scope of the invention, as defined by the claims.

The invention claimed is:

1. A process for performing a reductive amination of a chloro benzaldehyde organic feed substrate in the presence of hydrogen and a heterogeneous catalyst comprising palladium or platinum, and in absence of a catalytic amount of any second metal selected from the list consisting of silver, nickel, cobalt, tin, bismuth, copper, gold, and combinations thereof, whereby the heterogeneous catalyst has been heat-treated prior to the reductive amination at a temperature in the range of 100° C. to 600° C. for a period of at least one hour.

2. The process according to claim 1, comprising reductively aminating ortho-chloro-benzaldehyde with dimethyl amine in the presence of hydrogen and said catalyst to produce ortho-chloro benzyl dimethyl amine.

3. The process according to claim 1, wherein the reductive amination is performed in two steps, in the first step reacting the substrate, containing as the first functional group an aldehyde, with a nitrogen containing compound, and in the subsequent step introducing hydrogen and the catalyst.

4. The process according to claim 1, wherein the heterogeneous catalyst comprises the first metal at a concentration in the range of 0.1-10.0% by weight, based on the total weight of the catalyst and the second metal or combinations thereof at a concentration of at most 0.1% by weight, based on the total weight of the catalyst.

5. The process according to claim 1, wherein the heterogeneous catalyst has been heat treated at a temperature of at least 200° C. for at least 2 hours.

6. The process according to claim 1, wherein the heat treatment of the heterogeneous catalyst is performed by exposure of the catalyst to a flow of nitrogen at a WWH in the range of from 0.0200 to 2.0000 h$^{-1}$.

7. The process according to claim 6, wherein the heterogeneous catalyst at the start of the heat-treatment contains at most 5% wt free water.

8. The process according to claim 1, wherein the heterogeneous catalyst has been dried prior to the heat-treatment.

9. The process according to claim 1, wherein the heat treatment is performed in the presence of a liquid comprising the feed substrate, a solvent, or mixtures thereof.

10. The process according to claim 1, wherein the heterogeneous catalyst has a support comprising carbon, alumina, silica, zeolite, clay, porous polymer or a hybrid polymer.

11. The process according to claim 1, wherein the heterogeneous catalyst has an average metal particle size in the range of 2 to 20 nm.

12. The process according to claim 1, wherein the heterogeneous catalyst has been pre-reduced after the heat treatment and prior to the step of contacting the catalyst with the organic feed substrate by subjecting the catalyst to a hydrogen partial pressure of at least 5 bar absolute, during a period of at least 30 minutes and at a temperature of at least 120° C.

13. The process according to claim 1, wherein at least 80% of chlorine atoms on the feed substrate are retained after the conversion.

14. The process according to claim 1, wherein the reductive amination is performed at an $H_2$ partial pressure in the range of 0.01-250 bar gauge.

15. The process according to claim 1, wherein the reductive amination is performed in the presence of methanol.

16. The process according to claim 1, wherein said process produces ortho-chloro-benzyldimethylamine, further comprising a first step the preparation of making a Grignard reagent from the ortho-chloro-benzyldimethylamine by introducing a magnesium atom between the benzene ring of the ortho-chloro-benzyldimethylamine compound and its chlorine atom, followed by a second step wherein the Grignard reagent is esterified to make a methoximinophenylglyoxylic ester.

17. The process according to claim 16, further comprising the production of a fungicide including the methoximinophenylglyoxylic ester.

18. The process according to claim 17, further including the step of treating a surface with the fungicide containing the methoximinophenylglyoxylic ester.

19. The process according to claim 1, wherein the heterogeneous catalyst has been heat-treated prior to the reductive amination at a temperature in the range of 200° C. to 600° C. for a period of at least two hours.

20. The process according to claim 1, wherein the heterogeneous catalyst has been heat-treated, prior to the reductive amination, at a temperature in the range of 200° C. to 600° C. for a period of at least two hours.

21. The process according to claim 1, wherein the heterogeneous catalyst has been heat-treated prior to the reductive amination under a flow of nitrogen at a WWH rate at least 0.050 h$^{-1}$.

22. The process according to claim 1, wherein the heterogeneous catalyst has been heat-treated prior to the reductive amination under a flow of nitrogen at a WWH rate at least 0.075 h$^{-1}$.

23. The process according to claim 1, wherein the heterogeneous catalyst has been heat-treated prior to the reductive amination at a temperature within a range of 200° C. to 600° C. under a flow of nitrogen at a WWH rate at least 0.050 h$^{-1}$ for at least two hours.

24. The process according to claim 23, wherein the temperature is within a range of 300° C. to 600° C. and the WWH flow of nitrogen is at least 0.120 hr$^{-1}$.

25. The process according to claim 24, wherein the catalyst is dried at a temperature of less than 100° C. before said heat treatment step sufficient such that the catalyst, at the start of the heat treatment step, contains not more than 10 wt. % free water, based on the weight of the catalyst.

* * * * *